(12) United States Patent
Zucherman et al.

(10) Patent No.: US 6,746,485 B1
(45) Date of Patent: Jun. 8, 2004

(54) HAIR USED AS A BIOLOGIC DISK, REPLACEMENT, AND/OR STRUCTURE AND METHOD

(75) Inventors: James F. Zucherman, San Francisco, CA (US); Ken Y. Hsu, San Francisco, CA (US)

(73) Assignee: St. Francis Medical Technologies, Inc., Alameda, CA (US)

( * ) Notice: Subject to any disclaimer, the term of this patent is extended or adjusted under 35 U.S.C. 154(b) by 0 days.

(21) Appl. No.: 09/504,826

(22) Filed: Feb. 16, 2000

Related U.S. Application Data

(60) Provisional application No. 60/120,486, filed on Feb. 18, 1999, and provisional application No. 60/163,224, filed on Nov. 3, 1999.

(51) Int. Cl.$^7$ ................................................ A61F 2/44
(52) U.S. Cl. ................................................ 623/17.16
(58) Field of Search ........................... 623/17.16, 17.15, 623/17.12, 11.11, 15.11, 13.11, 13.19, 13.2, FOR 113, 901, 925, 66.1; 132/53

(56) References Cited

U.S. PATENT DOCUMENTS

| | | | |
|---|---|---|---|
| 1,364,366 A | | 1/1921 | Goldman |
| 2,677,369 A | | 5/1954 | Knowles |
| 2,865,380 A | | 12/1958 | Mithcell |
| 3,119,398 A | | 1/1964 | Bennett et al. |
| 3,867,728 A | * | 2/1975 | Stubstad et al. ......... 623/17.16 |
| 3,875,595 A | | 4/1975 | Froning |
| 4,309,777 A | | 1/1982 | Patil |
| 4,349,921 A | | 9/1982 | Kuntz |
| 4,599,086 A | | 7/1986 | Doty |
| 4,714,469 A | | 12/1987 | Kenna |
| 4,772,287 A | | 9/1988 | Ray et al. |
| 4,904,260 A | | 2/1990 | Ray et al. |
| 4,904,261 A | | 2/1990 | Dove et al. |
| 4,946,378 A | | 8/1990 | Hirayama et al. |
| 5,035,716 A | | 7/1991 | Downey |
| 5,047,055 A | | 9/1991 | Bao et al. |

(List continued on next page.)

FOREIGN PATENT DOCUMENTS

| | | |
|---|---|---|
| FR | 2717675 | 9/1995 |
| WO | WO 94/26192 | 11/1994 |
| WO | WO 98/48717 | 11/1998 |
| WO | WO 99/26562 | 6/1999 |
| WO | WO 99/42051 | 8/1999 |
| WO | WO 00/13619 | 3/2000 |
| WO | WO 00/13620 | 3/2000 |

OTHER PUBLICATIONS

Minns, R.J., et al., *Preliminary Design and Experimental Studies of a Novel Implant for Correcting Sagittal Plane Instability in the Lumbar Spine*, Spine vol. 22, No. 16, pp. 1819–1825, © 1997, Lippincott–Raven Publishers.

Haruo Tsuji, et al., *Ceramic Interspinous Block (CISB) Assisted Anterior Interbody Fusion*, Jounal of Spinal Disorders, vol. 3, No. 1, pp. 77–86, ©1990 Raven Press, Ltd., New York.

*Preliminary Studies on the Use of Nail as a Material for Reconstructive or Cosmetic Surgery*; Peter Taylor, Ph.Sc., and Garbis Kaakedjian, M.D., Laboratorji de Fisiopatologia, Centro de Medicina Experimental, Instituto Venezolano de Investigaciones Clentificas, Received for publication Mar. 10, 1997; revised May 27, 1997; pp. 1276–1279.

*Hair as a Filter Material for Reconstructive or Cosmetic Surgery*, Garbis Kaakedjian, M.D., and Peter Taylor, Ph.Sc., Laboratorji de Fisiopatologia, Centro de Medicina Experimental, Insituto Venezolano de Investigacions Clentificas, Received for publication Aug. 14, 1995; revised Jan. 26, 1996; pp. 443–447.

U.S. patent applicaiton Ser. No. 09/802,113, Van Dyke, et al, filed Mar. 8, 2001.

*Primary Examiner*—Alvin Stewart
(74) *Attorney, Agent, or Firm*—Fliesler Meyer LLP

(57) ABSTRACT

Hair is used as a biologic disk, replacement, and/or structure.

75 Claims, 4 Drawing Sheets

Hair disc implant comprised of multiple layers 22, 24, 26 of woven hair with each layer having a different orientation.

U.S. PATENT DOCUMENTS

| Patent | Date | Inventor |
|---|---|---|
| 5,123,926 A | 6/1992 | Pisharodi |
| 5,137,533 A | 8/1992 | Giampapa |
| 5,263,953 A | 11/1993 | Bagby |
| 5,306,309 A | 4/1994 | Wagner et al. |
| 5,358,935 A | 10/1994 | Smith et al. |
| 5,390,683 A | 2/1995 | Pisharodi |
| 5,443,514 A | 8/1995 | Steffee |
| 5,458,643 A | 10/1995 | Oka et al. |
| 5,505,732 A | 4/1996 | Michelson |
| 5,514,180 A | 5/1996 | Heggeness et al. |
| 5,534,028 A | 7/1996 | Bao et al. |
| 5,534,029 A | 7/1996 | Shima |
| 5,549,679 A | 8/1996 | Kuslich |
| 5,562,736 A | 10/1996 | Ray et al. |
| 5,609,634 A | 3/1997 | Voydeville |
| 5,634,945 A | 6/1997 | Pernia et al. |
| 5,667,961 A | 9/1997 | Bernard et al. |
| 5,674,295 A | 10/1997 | Ray et al. |
| 5,674,296 A | 10/1997 | Bryan et al. |
| 5,676,702 A | 10/1997 | Ratron |
| 5,766,252 A | 6/1998 | Henry et al. |
| 5,800,545 A | 9/1998 | Yamada et al. |
| 5,865,846 A | 2/1999 | Bryan et al. |
| 5,888,224 A | 3/1999 | Beckers et al. |
| 5,888,226 A | 3/1999 | Rogozinski |
| 5,932,552 A | 8/1999 | Blanchard et al. |
| 5,944,754 A | 8/1999 | Vacanti |
| 5,948,432 A | 9/1999 | Timmons et al. |
| 5,976,186 A | 11/1999 | Bao et al. |
| 6,001,130 A | 12/1999 | Bryan et al. |
| 6,022,376 A | 2/2000 | Assell et al. |
| 6,113,639 A | 9/2000 | Ray et al. |
| 6,156,067 A | 12/2000 | Bryan et al. |
| 6,371,984 B1 | 4/2002 | Van Dyke et al. ............ 623/11 |
| 6,379,690 B2 * | 4/2002 | Blanchard et al. .......... 424/422 |
| 6,416,776 B1 * | 7/2002 | Shamie ....................... 424/423 |
| 2002/0029083 A1 | 3/2002 | Zucherman |

* cited by examiner

HAIR USED AS A BIOLOGIC DISK, REPLACEMENT, AND/OR STRUCTURE AND METHOD

This application claims the benefit of U.S. Provisional Application No. 60/120,486, filed Feb. 18, 1999, and Provisional Application No. 60/163,224, filed Nov. 3, 1999.

FIELD OF THE INVENTION

The field of the invention relates to biologic disks, replacements, and/or structures principally for human and animal use.

BACKGROUND OF THE INVENTION

The normal human disk is made of multiple layers (13) of collagen and a highly hydrophilic mucopolysaccharide center. This is similar to a radial car tire. This construct converts compression axial loads on the gelatinous center to the outer collagen fibers as tensile forces. This tissue is highly viscoelastic. The construct provides both mobility and stability to the spinal joints. Unfortunately the chemical properties of the gelatinous center material (nucleus pulposis) deteriorate with age and become less hydrophilic. Forces are not converted from compression to tension as well and more compression and torsional loads are conferred to the outer layers (annulus). These layers deteriorate and lose their integrity forming multiple small tears, which coalesce and become large ones. The disk loses height; material bulges or extrudes into inappropriate locations through ruptured annular walls. The grip on the vertebra slackens and chronic nerve stimulation occurs due to release of degenerated debris and loss of space for the nerves. Thus we have 80% of the population with significant disabling symptoms at some time in their lives from lumbar spine disease. The only ailment more common than back pain is the common cold.

In orthopedic surgery badly deteriorated joints are either fused together to control pain or joint replacement procedures are performed to control pain without complete loss of the motion function of the joint. Obviously the maintaining of as much of the normal motion in the joint as is possible is ideal. When joints are fused, adjacent joints must work much harder in compensation, and may become symptomatic also. In the lumbar spine there are five joints and the hips that share in the motion function so there is more forgiveness when one or more, but fewer than when all, are fused together. However, very often there are several deteriorated joints. Fusing too many joint results in such overload of adjacent joint structures that as many problems are created by fusing as are solved. The treatment of hip and knee arthritis has been absolutely revolutionized by joint replacement surgery. The spine is still in the dark ages because of no viable joint replacement procedure exists.

The spinal joint is actually three joints, two facet joints and one disk. The three joints interact to allow the right balance of mobility and stability for spine function as we know it. Research has shown that deterioration occurs first in the disk, and then as a consequence of changes in the facet joints. Therefore, replacing the disk function will halt deterioration of the entire joint complex.

Much work has been done in order to develop mechanical disk replacements. None have been shown to have lasting effectiveness. Problems associated with maintaining the location, size, wear, and fatigue failure have been the stumbling blocks for prior prototypes.

SUMMERY OF THE INVENTION

A biologically compatible prosthesis will certainly be the future reality for disk replacement. Hair which is immunologically silent, strong, very modifiable and has the potential for biological incorporation is the answer. There are two components to the disk as mentioned above. These include the annulus and the nucleus pulposis. The former, in one embodiment, can be constructed similarly to a textile from autologous or homologous hair. The latter, in one embodiment, can be constructed by processing keratin sulfate or utilizing another substance such as a hydrophilic gel, poloyxymer 407, and/or regenerated in vivo by utilization of morphogenetic growth factors. Recombinant growth factors are being produced now and some do produce the same substances in the nucleus pulposis under appropriate conditions in vivo. One embodiment includes a "hair bag" inserted into the center of the human disk through a small incision and that is then filled with a gelatinous substance containing cartilage growth factors. As the body incorporates the tissue, the new somewhat similar "disk" forms within the deteriorated one. The tissue may be more fibrotic than normal, and have less elasticity than normal. This would nevertheless meet the goal of allowing motion and stability, and therefore greatly improve symptornatology.

Other aspects of the invention use hair as a biologic implant, replacement, and/or structure. Such implants can be cosmetic implants. Additional blood vessel replacements can be constructed from hair. Further, hair can be used for joint resurfacing or meniscal replacement. Still further, hair can be used as a biological endoprosthesis for ligament and tendons.

BRIEF DESCRIPTION OF THE FIGURES

FIG. 1 is attached.

FIG. 2 is attached.

DETAILED DESCRIPTION OF THE PREFERRED EMBODIMENTS

First Artificial Disk Structure

Figure 1:
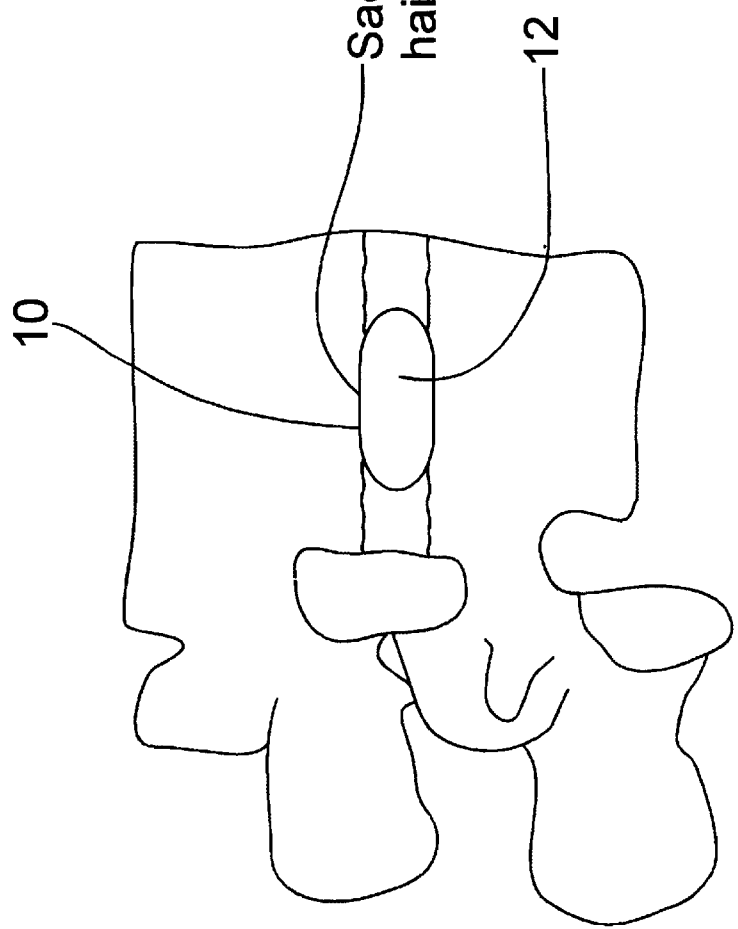
FIG. 1 is a representation of an embodiment of the first artificial disk structure of the invention with a polymer retained in a sack.

For this embodiment (FIG. 1), a state-temperature dependent polymer can be injected as a liquid into the diseased intervertebral disk, and then can undergo a change to a solid viscoelastic state a body temperature, which can have similar properties as the normal intervertebral disk. The polymer can include, by way of example any one of the following polymers. These polymers include Poloxamer 407 and other Poloxamers, polymer combinations, and polypropylene, These polymers can be acquired under the trade names Poloxamer 407, Plannemic-Acid F 127, from the following company: Sigma Aldrich. An outer covering to contain the artificial disk, which covering has sufficient tensile strength, will be necessary to maintain the disk height and prevent compression on the centrally injected polymer. Accordingly, a woven outer sack 10 can be used to reproduce the normal disk's function. This sack 10 would need to be biocompatible to facilitate ingrowth of normal fibrous or fibrocartilaginous tissue, anchoring and melding the artificial disk with remnants of living disk tissue and/or the vertebral bone. Possible candidates for this outer sheath are various polymer compounds, and the recipient's own hair processed to form a tightly woven fabric. The proteins in recipient's hair will not be subject to rejection phenomena and thus, be readily accepted by the recipient's immune system, a crucial factor for ingrowth to occur. Polymer materials which could be used to form the outer sack include: polypropylene, polylactic acid materials, polyesther polymer mesh, composites of collagen and BMP, titanium fiber with BMP with or without non-collagenase proteins, polydioxanone, polyphosphazenes and BMP, ceramic collagen composite, expanded polytetrafluoroethylene barrier membranes, and ethylene-vinyl acetate copolymers in methylene chloride (Elvax 40).

These polymers are characterized as having the following (physical, mechanical, chemical, biomechanical) properties and ranges of properties: good tensile strength, low coefficient of elasticity, capacity for soft tissue in growth or replacement in vivo, binding affinity for BMP, TGF-Beta, and other bone, fibrous and cartilage tissue growth factors, resistance to fracture, and biocompatability. If the recipient's hair is used as the outer sack, such hair would be treated according to the following process. This process includes one or a combination of the following: Heparin SO4 treatment, dextran, protease, elastase, collagenase, guanidine hydrochloride and lithium bromide exposure. The hair would be woven or blended together using one of the following techniques. These techniques include: denaturation, acid treatment, loom and machine weaving.

After a portions or all of a dysfunctional disk is removed, the sack can be insertedin the inter-discal space. The disk material can be removed using a number of techniques currently on the market. Thereafter, the sack 10 can, by way of example only, be inserted through a cannula in a minimally invasive technique in order to position the sack in the space between two adjacent vertebral bodies. After this procedure is complete, the sack 10 can be injected and filled with the appropriate polymer 12 or other material. These materials can be state-dependent such that at one temperature, which is different than that of the body temperature of the patient, the materials flow more easily through a needle or cannula, and at about body temperature the materials become more able to support the weight along the spinal column. Thus the materials can become more viscous and resilient once attaining the temperature of the body of the patient.

As described above, in this embodiment, the sack is comprised of woven hair which is then filled with a polymer.

Second Artificial Disk Structure

Figure 2:
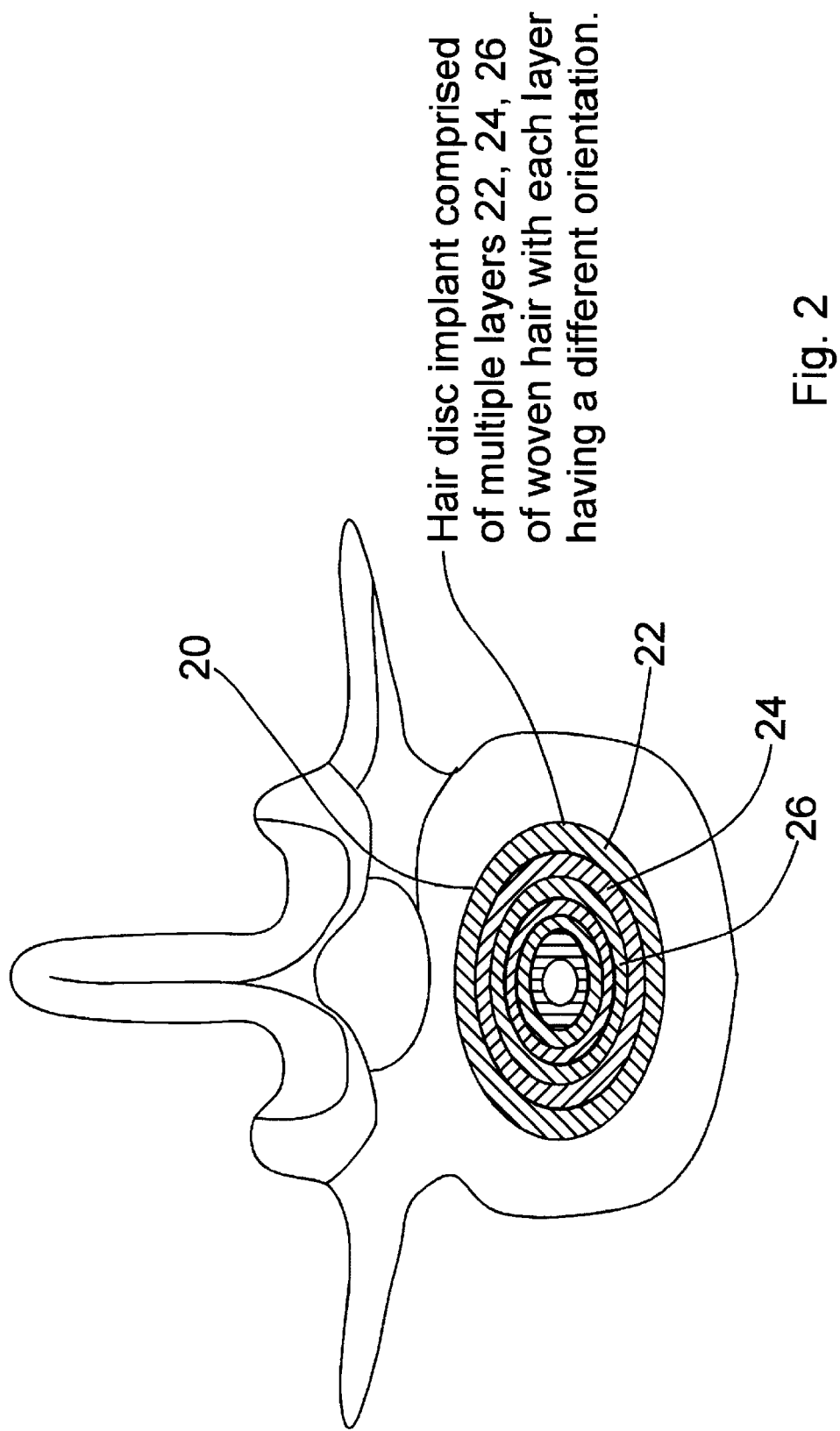
FIG. 2 is a representation of an embodiment of the second artificial disk structure of the invention with a disk comprised of hair with the hair in the center of the artificial disk specially treated to model the complex polymer found in a natural disk.
Figure 4:
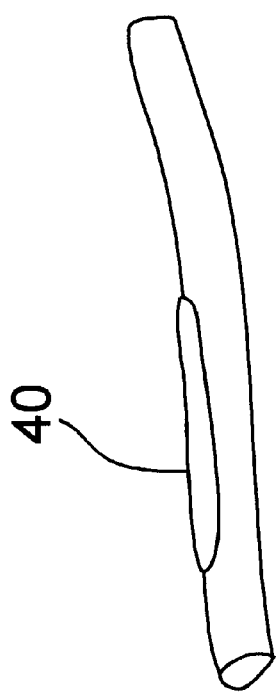
FIG. 4 is an embodiment of a vascular graph of the invention.
Figure 3:
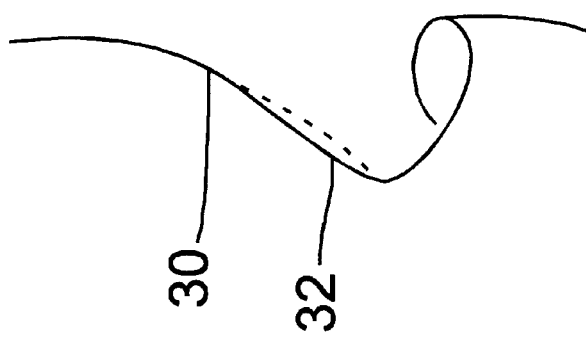
FIG. 3 is a representation of an embodiment of a cosmetic prosthesis for a nose.
Figure 6:
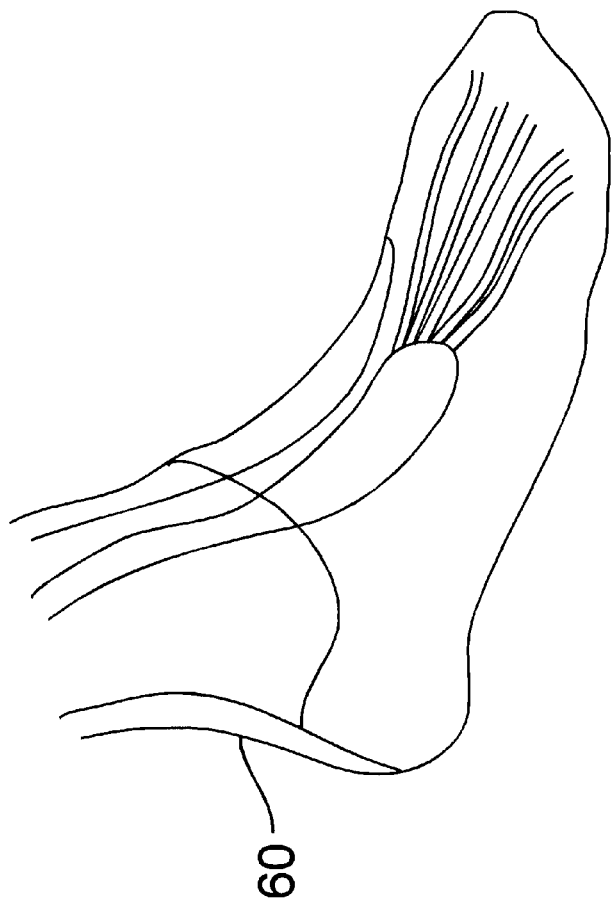
FIG. 6 is an embodiment of a tendon or ligament graph of the invention.
Figure 5:
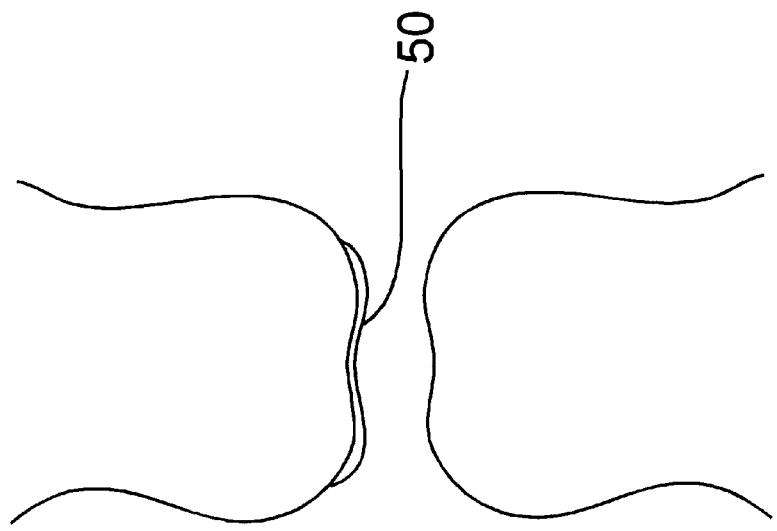
FIG. 5 is an embodiment of a joint resurfacing graph of the invention.

For this embodiment (FIG. 2), a disk replacement 20 is made of processed hair entirely. The process for processing the hair is as follows. This process includes one or more of the following: steps of denaturation, collagenase, protease, heparin sulphate, and dextran exposure. The hair can then be woven together in a mass and inserted into the disk space using a variety of techniques including from open surgery to insertion through an appropriately sized cannula. The hair can be a matrix structure characterized and described as follows. The matrix structure can include a denaturation, reduction of disulfide bonds (cyanogen bromide) proteolysis. Although not required for this embodiment, augmentation with cartilage producing Bone Morphogenic Protein (BMP) can allow a new intervertebral disk to form with the hair based collagen matrix as the cartilage inductive morphogenic substances and biomechanical stresses in the intervertebral space can induce differentiation of a new living intervertebral disk. Such Bone Morphogenic Protein can include the following types BMP's 1–15, TGF-Beta, insulin-like growth factor, platelet derived growth factor. Additionally, the complex organic polymer which makes up much of the center of the normal disk and is responsible for its properties can be chemically created from hair and processed collagen to use as the central matrix of the artificial disk. A process for treating the hair based collagen matrix, in order to create the central nucleus of the artificial disk is as follows. This method includes one or more of the following steps of heparin sulphate or other polyanionic compound denaturation, and guanidine hydrochloride exposure. An outer woven hair bag would still be used in this case to confer the necessary biomechanical properties. This hair bag or sack can be constructed and have the properties of the sack previously described above. In this embodiment, the basic disk implant is comprised of multiple layers 22, 24, 26 of woven hair with each layer having a different orientation.

The chemical processing of hair to modify its structure for use as (i) a Morphogenic protein carrier, and to (ii) increase its flexibility so it can be used as a strong "net' for use as a annulus replacement is as follows: This process includes mechanical weaving, partial denaturation, heparin treatment, collagenase and proteolytic treatment.

BMP (a cartilage and bone growth factor), in a particular embodiment can be carried by a product known as Poloxamer 407. The characteristics of this material are found in Table 1 below.

TABLE 1

Pluracare ® F 127 Prill
CTFA/INCI: Poloxamer 407

| Specifications | |
|---|---|
| Cloud Point (10% aqueous, ° C.) | ≧100 |
| Color (APHA) | ≦120 |
| Water Content (%) | ≦0.75 |
| pH (2.5% aqueous) | 6.0 to 7.4 |

| Description | Product Number |
|---|---|
| PluracareF 127 surfactant is a block copolymer of ethylene glycol and propylene glycols | 547427 |

| Appearance |
|---|
| White solid in the form of small beads |

| Solubility |
|---|
| Water soluble |

| Application |
|---|

Due to their low skin and eye irritation, the Pluracare grades find particular application in the cosmetic industry.
Pluracare F 127 is used as a solubilizer and emulsifier in a wide variety of areas from cosmetics to oral care products. At concentrations of about 20% in water it forms stable, clear, ringing gels in which a wide variety of ingredients can be incorporated. It is also used as a solubilizer.
Its HLB is in the range of 18 to 23.
CAS Number: 9003-11-6
Molecular Weight: ~12,600

TABLE 1-continued

Pluracare ® F 127 Prill
CTFA/INCI: Poloxamer 407

Manufacture: BASF Corporation, 3000 Continental Drive, North, Mount Olive, New Jersey 07826-1234

A specific example of Poloxamer used as a BMP carrier is found 35 in Table 2. Table 2 demonstrates a method that has successfully caused BMP to be injected into animal subjects and create cartilage and bone growth. Specific results of this example include formation of a mature ossicle of bone with bone Marrow cells in the middle of the injection site. The response was dose related.

TABLE 2

Poloxamer 407 as a Carrier for BMP

Materials & Method

1. A 25 w/w % Poloxamer 407 was prepared by adding sterile water to it in a beaker at 3° Celsius temperature
2. Magnetic stirrer was used until Poloxamer had dissolved in the solute
3. Aliquots of 1 cc was withdrawn in six syringes and poured in six vortex tubes
4. Two of each 2 mg, 5 mg, 10 mg hBMP (human native Bone Morphogenic Protein) samples were added to each vortex tube
5. The tubes were vortexed until the hBMP had distributed evenly in the solute
6. The contents of each vortex tube were injected in a mouse hindquarter muscle
7. The mice were sacrificed at 21 days and radiographic/histologic evaluations were performed From the above it can be appreciated that animal hair can be a carrier for BMP. Additionally Poloxamer 407 and similar compounds can be a carrier for BMP. Further Poloxamer 407 and similar compounds can be used as a BMP carrier in conjunction with the use of hair to make an artificial disk. The BMP in such an arrangement would create bone and cartilage on the outer periphery of the artificial disk in order to assist the artificial disk to bond with the upper and lower vertebral bodies which border the disk space. Additionally the BMP can assist the artificial disk to form an artificial nucleus.

Additionally in another embodiment of the invention Poloxamer 407 and like compounds can be used as a film, a gel, or a fluid in order to prevent post surgical adhesions. This material is prepared as follows in a preferred embodiment in order to be positioned adjacent to a surgical site and be effective an anti-adhesion material. The method for preparing this compound is as follows: 25% gel of Poloxamer 407 prepared by weighing 25 grams of poloxamer crystal in a beaker and adding distilled $H_2O$ in a cold room at less than 3° C. to bring the weight to 100 grams. Magnetic stirrer is used until a homogenous liquid is obtained. This will form a gel at room temperature.

Examples of BMP which can be used with the present invention can be obtained from a review of U.S. Pat. Nos. 4,563,489; 4,857,456; 4,795,804; all of which are incorporated herein by reference. Other examples for the promotion of bone growth can be found in the following US Patents all of which are incorporated herein by reference: U.S. Pat. Nos. 5,531,791 and 5,484,601. Additionally polylactic acid can be used as a BMP carrier for the above disk replacement embodiments, as well as Gelfoam®, collagen, polyester polymer mesh, composites of collagen and BMP, titanium fiber with BMP with or without non-collagenase proteins, polydioxanone, polyphosphazenes and BMP, ceramic collagen composite, expanded polytetrafluoroethylene barrier membranes, ethylene-vinyl acetate copolymers in methylene chloride (Elvax 40), composites of human fibrin, BMP/NCP in a polymethacrylate delivery system, sintered biodegradable b-tricalcium phosphate, composites of BMP and synthetic hydroxdyapatite mesh, hydroxy apatite adsorbed BMP, calcium sulphate, polylactic acid polymer composites, composites of poly-D (lactide coglycolide, and composites of e-caprolactone, high molecular weight polylactic acid homopolymers, composites of poly-2-hydroxyethyl methacrylate sponge, composites of polysulfone, polydioxanone, polyphosphazenes, cyanoacrylate, squalene, calcium glycerophosphoric acid, dextran, carbon, collagen type 1, and methyl pyrrolidinone.

Hair as a Biologic Cosmetic Implant

Xenograft, homologous or autologous pair is an ideal cosmetic endoprosthesis 32 for breast, lip, muscle, nose 30, buttock, eyes chest, calves and thighs. The strength, immunologic compatibility, and modifiable characteristics of hair and keratin sulfate make it ideal as an adjunct to plastic surgery. Current implants are associated with stiffening and capsule formation after implantation resulting in less than natural cosmetic results. Extensive debate regarding autoimmune disorders as a result of silicone implants would be obviated since the recipients own hair protein is recognized by the their bodies own immune system. Various gels can be manufactured from hair protein, which have similarity in physical characteristics to connective tissue fat and hydrophilic gels. The tensile strength of hair fibers can be used for maintenance of structural integrity to match body contours.

As with hair utilized as an intervertebral disk implant, various treatments are available to modify hair in order to obtain desirable structural characteristics. These include heparin sulfate, hydrolysis, lithium bromide, hydroxylation, sulfating, alkalinization and acidification. Impregnation with morphogenetic growth factors can also be utilized.

Hair and Keratin Sulfate as a Biological Endoprosthesis for Blood Vessel Replacement Autologous, homologous or xenograft hair is an ideal vascular graft 40 for arterial or venous replacement. It has the strength, compliance, immunological compatibility, flexibility, and ease of weaving into the appropriate structure. Autologous or allograft implants have minimal immunologic reactivity. The appropriate porosity of woven hair allows real endothelial growth. Hair can be woven or structured to have the compliance that is not present in the other grafts and can approximate normal vascular walls. The hair implant can be easily sutured to adjacent structures, because of the above characteristics. Patency of the hair vascular graft can be maintained. Hair can also be a part of the composite graft.

Hair as Joint Resurfacing or Meniscal Replacement

Autologous, allograft or xenograft hair is an appropriate implant for joint resurfacing and replacement for a meniscus. Hair can be woven and shaped into a different shape, size and porosity to fit human joints. It is immunologically compatible. It allows ingrowth of native cells into a woven structure. A hair graft 50 can easily be sutured to adjacent structures. It absorbs shock and stress well. Hair can be treated to form an elastomer. Hair can be fashioned into appropriate joint surfaces with reduced friction when compared to synthetic grafts.

Hair as a Biological Endoprosthesis for Ligaments and Tendons

Autologous, homologous (allograft) or xenograft hair is an appropriate tendon or ligament graft 60. Hair can be woven into strong structures. It remains flexible. The hair graft can be easily sutured to adjacent structures. The porosity of woven hair allows ingrowth of native tissues. The immunological compatibility, strength, flexibility and modifiable characteristics of hair are ideal for ligament and tendon replacement.

Industrial Applicability

Accordingly, the present invention can be used as a biologic disk, replacement, and/or structure.

Other features, aspects and objects of the invention can be obtained from a review of the figures and the claims.

It is to be understood that other embodiments of the invention can be developed and fall within the spirit and scope of the invention and claims.

We claim:

1. A replacement for at least part of a vertebral disk, the replacement comprising hair formed into a sack with keratin sulfate placed in the sack.

2. A replacement for at least part of a vertebral disk, the replacement comprising hair formed into a sack with a hydrophilic gel placed in the sack.

3. A replacement for at least part of a vertebral disk, the replacement comprising hair formed into a sack with the sack at least partially surrounding at least one of a hydrogel, a hydrophilic gel, keratin sulfate, and a growth factor.

4. A replacement for at least part of a vertebral disk, the replacement comprising hair formed into a sack with the sack at least partially surrounding a cartilage growth factor.

5. A replacement for at least part of a vertebral disk, the replacement comprising hair formed into a sack with at least some of which has been processed as keratin sulfate.

6. A replacement for at least part of a vertebral disk, the replacement comprising hair formed into a sack; and
wherein a cartilage growth factor is applied to said hair.

7. A replacement for at least part of a vertebral disk, the replacement comprising hair formed into a sack; and
wherein BMP is applied to said hair.

8. A replacement for at least part of a vertebral disk, the replacement comprising hair formed into a sack; and
wherein one or more morphogenetic growth factors is applied to said hair.

9. A replacement for at least part of a vertebral disk, the replacement comprising hair formed into a sack; and
wherein one or more recombinant growth factors is applied to said hair.

10. A replacement for at least part of a vertebral disk, the replacement comprising hair formed into a sack;
wherein an outer surface of the sack is covered with a polymer material; and
wherein said polymer material can include at least one of the group consisting of polypropylene, polylactic acid materials, polyesther polymer mesh, composites of collagen and BMP, titanium fiber with BMP with or without non-collagenase proteins, polydioxanone, polyphosphazenes and BMP, ceramic collagen composite, expanded polytetrafluoroethylene barrier membranes, and ethylene-vinyl acetate copolymers in methylene chloride (Elvax 40).

11. A replacement for at least part of a vertebral disk, the replacement comprising hair formed into a sack; and
wherein said hair is treated with at least one of the group consisting of: heparin, dextran, protease, elastase, collagenase, guanidine hydrochloride, and lithium bromide.

12. A replacement for at least part of a vertebral disk, the replacement comprising hair; and
wherein the replacement is comprised of said hair formed into a sack; and wherein said sack is filled with a material which has a state dependent upon the temperature of the material.

13. The replacement of claim 12 comprised of human hair.

14. The replacement of claim 12 comprised of woven hair.

15. The replacement of claim 12 comprised of matted hair.

16. The replacement of claim 12 wherein said hair is formed into a replacement annulus.

17. The replacement of claim 12 wherein said hair is used to construct in a replacement annulus.

18. The replacement of claim 12 wherein said hair is one of autologous hair and homologous hair.

19. The replacement of claim 12 wherein said hair is one of autogeneic hair and allogeneic hair.

20. The replacement of claim 12 wherein said sack at least partially surrounds a cartilage growth factor.

21. The replacement of claim 12 wherein said sack surrounds hair treated to model a natural disk.

22. The replacement of claim 12 wherein the replacement is comprised of at least two layers of said hair.

23. The replacement of claim 12 wherein the replacement is comprised of at least a first layer of woven hair and a second layer of woven hair.

24. The replacement of claim 23 wherein the hair in the first layer has a different orientation than the hair in the second layer.

25. The replacement of claim 12 wherein a cartilage growth factor is applied to said hair.

26. The replacement of claim 12 wherein BMP is applied to said hair.

27. The replacement of claim 12 wherein one or more morphogenetic growth factors is applied to said hair.

28. The replacement of claim 12 wherein one or more recombinant growth factors is applied to said hair.

29. The replacement of claim 12 wherein outer surface of the sack is covered with a polymer material.

30. The replacement of claim 29 wherein said polymer material can include at least one of the group consisting of polypropylene, polylactic acid materials, polyesther polymer mesh, composites of collagen and BMP, titanium fiber with BMP with or without non-collagenase proteins, polydioxanone, polyphosphazenes and BMP, ceramic collagen composite, expanded polytetrafluoroethylene barrier membranes, and ethylene-vinyl acetate copolymers in methylene chloride (Elvax 40).

31. The replacement of claim 12 wherein said hair is treated with at least one of the group consisting of: heparin, dextran, protease, elastase, collagenase, guanidine hydrochloride, and lithium bromide.

32. The replacement of claim 12 wherein said hair is woven and/or blended together using at least one of the following techniques consisting of: matting, denaturation, acid treatment, and weaving.

33. The replacement of claim 12 wherein said hair is treated with one or more bone growth factors.

34. The replacement of claim 12 comprised of hair at least some of which has been processed as keratin sulfate.

35. The replacement of claim 12 wherein said sack contains one or more bone growth factor materials.

36. A replacement for at least part of a vertebral disk, the replacement comprising hair; and
 wherein the replacement is comprised of said hair formed into a sack; and
 wherein said sack is filled with a material; and
 wherein said material becomes at least one of more viscous and resilient when the material reaches the temperature of a patient's body.

37. The replacement of claim 36 comprised of human hair.

38. The replacement of claim 36 comprised of woven hair.

39. The replacement of claim 36 comprised of matted hair.

40. The replacement of claim 36 wherein said hair is formed into a replacement annulus.

41. The replacement of claim 36 wherein said hair is used to construct in a replacement annulus.

42. The replacement of claim 36 wherein said hair is one of autologous hair and homologous hair.

43. The replacement of claim 36 wherein said hair is one of autogeneic hair and allogeneic hair.

44. The replacement of claim 36 wherein said sack at least partially surrounds a cartilage growth factor.

45. The replacement of claim 36 comprised of hair in the center of the sack treated to model a natural disk.

46. The replacement of claim 36 wherein the sack is comprised of at least two layers of said hair.

47. The replacement of claim 36 wherein the sack is comprised of at least a first layer of woven hair and a second layer of woven hair.

48. The replacement of claim 47 wherein the hair in the first layer has a different orientation than the hair in the second layer.

49. The replacement of claim 36 wherein a cartilage growth factor is applied to said hair.

50. The replacement of claim 36 wherein BMP is applied to said hair.

51. The replacement of claim 36 wherein one or more morphogenetic growth factors is applied to said hair.

52. The replacement of claim 36 wherein one or more recombinant growth factors is applied to said hair.

53. The replacement of claim 36 wherein an outer surface of the sack is covered with a polymer material.

54. The replacement of claim 53 wherein said polymer material can include at least one of the group consisting of polypropylene, polylactic acid materials, polyesther polymer mesh, composites of collagen and BMP, titanium fiber with BMP with or without non-collagenase proteins, polydioxanone, polyphosphazenes and BMP, ceramic collagen composite, expanded polytetrafluoroethylene barrier membranes, and ethylene-vinyl acetate copolymers in methylene chloride (Elvax 40).

55. The replacement of claim 36 wherein said hair is treated with at least one of the group consisting of: heparin, dextran, protease, elastase, collagenase, guanidine hydrochloride, and lithium bromide.

56. The replacement of claim 36 wherein said hair is woven and/or blended together using at least one of the following techniques consisting of: matting, denaturation, acid treatment, and weaving.

57. The replacement of claim 36 wherein said hair is treated with one or more bone growth factors.

58. The replacement of claim 36 comprised of hair at least some of which has been processed as keratin sulfate.

59. The replacement of claim 36 wherein said sack contains one or more bone growth factor materials.

60. A replacement for at least part of a vertebral disk, the replacement comprising hair formed into a sack; and
 wherein said hair is treated with one or more bone growth factors.

61. A replacement for at least part of a vertebral disk, the replacement comprising hair formed into a sack; and
 wherein said sack is filled with one or more bone growth factor materials.

62. A method of delivering a disk prosthetic device to an intervertebral space comprising the steps of:
 first delivering a disk prosthetic device comprised in part of hair to the intervertebral space said disk prosthetic device formed into a sack; and
 second delivering a filling material to the disk prosthetic device.

63. A replacement for at least part of a vertebral disk, the replacement comprising hair;
 wherein the replacement is comprised of at least a first layer of woven hair and a second layer of woven hair;
 wherein the hair in the first layer has a different orientation than the hair in the second layer; and
 wherein the hair formed into a sack with keratin sulfate placed in the sack.

64. A replacement for at least part of a vertebral disk, the replacement comprising hair;
 wherein the replacement is comprised of at least a first layer of woven hair and a second layer of woven hair;
 wherein the hair in the first layer has a different orientation than the hair in the second layer; and
 wherein the hair is formed into a sack with a hydrophillic gel placed in the sack.

65. A replacement for at least part of a vertebral disk, the replacement comprising hair;
 wherein the replacement is comprised of at least a first layer of woven hair and a second layer of woven hair;
 wherein said hair in the first layer has a different orientation than said hair in the second layer; and
 wherein said hair is formed into a structure with the structure at least partially surrounding a cartilage growth factor.

66. A replacement for at least part of a vertebral disk, the replacement comprising hair;
 wherein the replacement is comprised of at least a first layer of woven hair and a second layer of woven hair;
 wherein the hair in the first layer has a different orientation than the hair in the second layer; and
 wherein the hair at least some of which has been processed at keratin sulfate.

67. A replacement for at least part of a vertebral disk;
 wherein the replacement is comprised of at least a first layer of woven hair and a second layer of woven hair;
 wherein the hair in the first layer has a different orientation than the hair in the second layer; and
 wherein a cartilage growth factor is applied to said hair.

68. A replacement for at least part of a vertebral disk;
 wherein the replacement is comprised of at least a first layer of woven hair and a second layer of woven hair;
 wherein the hair in the first layer has a different orientation than the hair in the second layer; and
 wherein BMP is applied to said hair.

69. A replacement for at least part of a vertebral disk;
 wherein the replacement is comprised of at least a first layer of woven hair and a second layer of woven hair;
 wherein the hair in the first layer has a different orientation than the hair in the second layer; and
 wherein one or more morphogenetic growth factors is applied to said hair.

70. A replacement for at least part of a vertebral disk;

wherein the replacement is comprised of at least a first layer of woven hair and a second layer of woven hair;

wherein the hair in the first layer has a different orientation than the hair in the second layer; and wherein one or more recombinant growth factors is applied to said hair.

71. A replacement for at least part of a vertebral disk;

wherein the replacement is comprised of at least a first layer of woven hair and a second layer of woven hair;

wherein the hair in the first layer has a different orientation than the hair in the second layer; and wherein said hair is formed into a sack and the outer surface of the sack is covered with a polymer material.

72. The replacement of claim 71 wherein said polymer material can include at least one of the group consisting of polypropylene, polylactic acid materials, polyesther polymer mesh, composites of collagen and BMP, titanium fiber with BMP with or without non-collagenase proteins, polydioxanone, polyphosphazenes and BMP, ceramic collagen composite, expanded polytetrafluoroethylene barrier membranes, and ethylene-vinyl acetate copolymers in methylene chloride (Elvax 40).

73. A replacement for at least part of a vertebral disk;

wherein the replacement is comprised of at least a first layer of woven hair and a second layer of woven hair;

wherein the hair in the first layer has a different orientation than the hair in the second layer; and wherein said hair is treated with at least one of the group consisting of: heparin, dextran, protease, elastase, collagenase, guanidine hydrochloride, and lithium bromide.

74. A replacement for at least part of a vertebral disk;

wherein the replacement is comprised of at least a first layer of woven hair and a second layer of woven hair;

wherein the hair in the first layer has a different orientation than the hair in the second layer; and wherein said hair is treated with one or more bone growth factors.

75. A replacement for at least part of a vertebral disk, the replacement comprised of hair formed in to a sack;

wherein the replacement is comprised of at least a first layer of woven hair and a second layer of woven hair;

wherein the hair in the first layer has a different orientation than the hair in the second layer; and wherein said sack is filled with one or more bone growth factor materials.

* * * * *